United States Patent [19]

Kiener et al.

[11] Patent Number: 5,622,846
[45] Date of Patent: Apr. 22, 1997

[54] BIOTECHNOLOGICAL PROCESS FOR THE PREPARATION OF CYCLIC-S-α-IMINO CARBOXYLIC ACIDS AND R-α-IMINO CARBOXAMIDES

[75] Inventors: Andreas Kiener, Visp; Jean-Paul Roduit, Gröne; Jörg Kohr, Raron; Nicholas Shaw, Visp, all of Switzerland

[73] Assignee: Lonza AG, Basel, Switzerland

[21] Appl. No.: 478,960

[22] Filed: Jun. 7, 1995

[30] Foreign Application Priority Data

Jun. 9, 1994 [CH] Switzerland ............................ 1813/94
Jul. 13, 1994 [CH] Switzerland ............................ 2231/94

[51] Int. Cl.$^6$ ................................................ C12P 13/00
[52] U.S. Cl. .................. 435/128; 435/252.1; 435/252.3; 435/852; 435/877; 435/878
[58] Field of Search ............................ 435/252.1, 253.3, 435/128, 852, 877, 878

[56] References Cited

PUBLICATIONS

M.C. Ng-Youn Chen et al., "Kinetic Resolution of Pipecolic Acid [. . . ]", *J. Org. Chem.*, 1994, vol. 59, pp. 2075–2081.
J.W. Huh et al., "Total Conversion of Racemic Pipecolic Acid [. . . ]", *Biosci. Biotech. Biochem.*, 1992, vol. 56, pp. 2081–2082.
J.W. Huh et al., "Synthesis of L–Proline [. . . ]", *Journal of Fermentation and Bioengineering*, 1992, vol. 74, pp. 189–190.

*Primary Examiner*—Herbert J. Lilling
*Attorney, Agent, or Firm*—Brumbauge, Graves, Donohue & Raymond

[57] ABSTRACT

Microorganisms of interest are capable of utilizing α-imino carboxamides, in the form of the racemate or of its optically active isomers, of the general formula

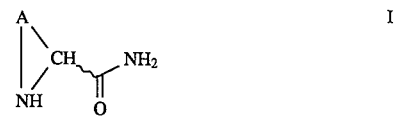

wherein A together with —NH— and —CH— is an optionally substituted 5- or 6-membered saturated heterocyclic ring, as sole nitrogen source, and converting (RS)-α-imino carboximides of Formula I into an S-α-amino carboxylic acid of the general formula

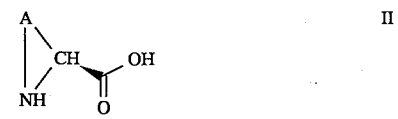

These microorganisms are useful also for biconversion of an (RS)-α-imino carboxamide of Formula I into an S-α-amino carboxylic acid.

2 Claims, No Drawings

BIOTECHNOLOGICAL PROCESS FOR THE PREPARATION OF CYCLIC-S-α-IMINO CARBOXYLIC ACIDS AND R-α-IMINO CARBOXAMIDES

BACKGROUND OF THE INVENTION

The invention relates to microorganisms which are capable of producing an S-α-imino carboxylic acid of the general formula

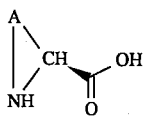

where A together with —NH— and —CH— is an optionally substituted 5- or 6-membered saturated heterocyclic ring.

S-α-imino carboxylic acids of Formula II, e.g., S-α-pipecolic acid are important intermediates for the preparation of numerous bioactive compounds, e.g., thioridazine or pipradol (Ng-Youn-Chen et al., J. Org. Chem., Vol. 59, No. 8, 1994).

In addition to numerous chemical racemate resolutions of (RS)-pipecolic acid and its derivatives, biotechnological racemate resolutions are also known. For example, Huh et al., Biosci., Biotech. Biochem., 56(12), 2081–2082 describe the racemate resolution of (RS)-pipecolic acid using an R-amino-acid oxidase. This entails specific oxidation of the R-isomer to $\Delta^1$-piperideine-2-carboxylic acid, resulting in S-pipecolic acid. After chemical reduction of the $\Delta^1$-piperideine-2-carboxylic acid to (RS)-pipecolic acid, the action of the R-amino-acid oxidase again results in S-pipecolic acid. This involves a continual decrease in the content of R-pipecolic acid. An analogous process for preparing S-proline is described in J. Ferm. Bioeng., 74, 189–190, 1992. However, these two processes have the disadvantage of not being practicable on a commercial scale. Another disadvantage is in that purified R-amino-acid oxidase must be used.

It is known further that racemic pipecolic esters are converted under the action of a lipase from *Aspergillus niger* into S-pipecolic acid and R-pipecolic esters (Ng-Youn-Chen et al., 1994, ibid.). However, this process has the disadvantage of S-pipecolic acid being obtained with an enantiomeric purity of only ee=93%.

SUMMARY OF THE INVENTION

It is an object of the present invention to provide a convenient, commercially practicable biotechnological process for the preparation of cyclic S-α-imino carboxylic acids and to isolate the latter in good enantiomeric purity.

Microorganisms of the invention are capable of utilizing α-imino carboxamides, in the form of the racemate or of its optically active isomers, of the general formula

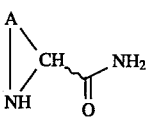

where A together with —NH— and —CH— is an optionally substituted 5- or 6-membered saturated heterocyclic ring, as sole nitrogen source, and of converting (RS)-α-imino carboxamides of Formula I into an S-α-imino carboxylic acid of the general formula

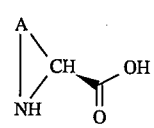

These microorganisms and their cell-free enzymes are used for a novel process for the preparation of S-α-imino carboxylic acids (Formula II) and/or for the preparation of R-α-imino carboxamides of the general formula

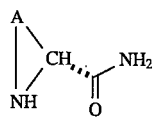

DETAILED DESCRIPTION OF PREFERRED EMBODIMENTS

Microorganisms according to the invention can be isolated from soil samples, sludge or waste water with the assistance of conventional microbiological techniques. According to a preferred embodiment of the invention, the microorganisms are isolated by a) cultivating them in a medium with an α-amino carboxamide (Formula I) in the form of the racemate or of its optically active isomers as sole nitrogen source and with a suitable carbon source in a conventional way, and b) selecting from the resulting culture those which are stable and are capable of converting (RS)-α-amino carboxamide (Formula I) into an S-α-amino carboxylic acid (Formula II).

It is thus possible to use all those microorganisms which contain these S-imino-acid amidases. It is convenient to select microorganisms which utilize piperazinecarboxamide or pipecolamide, in the form of the racemate or of the optically active isomers, as sole nitrogen source. It is preferable to select those which utilize S-piperazinecarboxamide or S-pipecolamide as sole nitrogen source.

The microorganisms are able to utilize as carbon source, e.g., sugars, sugar alcohols, carboxylic acids or alcohols as growth substrate. Sugars which can be used are hexoses, e.g., glucose or pentoses. Carboxylic acids which can be used are di- or tricarboxylic acids or the salts thereof, e.g., citric acid or succinate. It is possible to use as alcohol a trihydric alcohol, e.g., glycerol. A trihydric alcohol, e.g., glycerol is preferably used as carbon source.

The selection medium and culture medium can be those normally used by skilled workers, e.g., the mineral salt medium of Kulla et al. (Arch. Microbiol., 135, 1–7, 1983) or, preferably, that described in Table 1.

The active enzymes of the microorganisms are conveniently induced during the cultivation and selection. It is possible to use as enzyme inducer, e.g., piperazinecarboxamide, pipecolamide or acetamide.

Cultivation and selection conveniently take place at a temperature of 15°–50° C., preferably of 20°–45° C., and at a pH between pH 5 and pH 10, preferably between pH 6 and pH 9.

Preferred microorganisms with specific S-amino-acid amidase activity are piperazinecarboxamide-utilizing microorganisms of the genus Klebsiella, in particular of the species *Klebsiella pneumoniae* with the number DSM 9175 and 9176, or of the species *Klebsiella terrigena* with the number DSM 9174, and their functionally equivalent variants and mutants. These microorganisms were deposited on Apr. 24, 1994 at the Deutsche Sammlung von Mikroorganismen und Zellkulturen GmbH, Mascheroderweg 1b, D-38124 Braunschweig, in accordance with the Budapest Treaty.

Further suitable microorganisms are pipecolamide-utilizing microorganisms of the genus Pseudomonas, in particular of the species *Pseudomonas putida* with the number DSM 9923, or of the species *Pseudomonas fluorescens* with the number DSM 9924, and their functionally equivalent variants and mutants. These microorganisms were deposited on Apr. 20, 1994 at the Deutsche Sammlung von Mikroorganismen und Zellkulturen GmbH, Mascheroderweg 1b, D-38124 Braunschweig, in accordance with the Budapest Treaty.

"Functionally equivalent variants and mutants" are understood as microorganisms which have essentially the same properties and functions as the original microorganisms. Variants and mutants of this type can be produced by chance, by UV irradiation, for example.

Scientific description of microorganism DSM 9175 identified as *Klebsiella pneumoniae*:

| Properties of the strain Cell form | Rods |
|---|---|
| width μm | 0.8–1.0 |
| length μm | 1.0–3.0 |
| Motility | − |
| Gram reaction | − |
| Lysis by 3% KOH | + |
| Aminopeptidase (Cerny) | + |
| Spores | − |
| Oxidase | − |
| Catalase | + |
| Growth anaerobic | + |
| Acid from (OF test) | |
| glucose aerobic | + |
| glucose anaerobic | + |
| Gas from glucose | + |
| Acid from (ASA) | |
| glucose | + |
| fructose | + |
| xylose | + |
| erythritol | − |
| adonitol | + |
| D-mannose | + |
| L-rhamnose | + |
| dulcitol | − |
| inositol | + |
| sorbitol | + |
| α-methyl-D-glucoside | + |
| cellobiose | + |
| maltose | + |
| lactose | + |
| L-sorbose | − |
| L-fucose | − |
| D-arabitol | + |
| ONPG | + |
| ADH | − |
| LDC | + |
| ODC | − |
| VP | + |
| indole | − |
| H$_2$S production | − |
| Simmons citrate | + |
| phenylalanine deaminase | − |
| urease | − |
| hydrolysis of gelatin | − |
| DNA | − |

Abbreviations:
ASA = acetylsalicyclic acid
OF = Oxidation fermentation
ONPG = O-nitrophenyl galactosidase
ADH = alcohol dehydrogenase
VP = Voges Proskauer Scientific description of microorganism DSM 9176 identified as *Klebsiella pneumoniae*:

| Properties of the strain Cell form | Rods |
|---|---|
| width μm | 0.8–1.0 |
| length μm | 1.0–3.0 |
| Motility | − |
| Gram reaction | − |
| Lysis by 3% KOH | + |
| Aminopeptidase (Cerny) | + |
| Spores | − |
| Oxidase | − |
| Catalase | + |
| Growth anaerobic | + |
| Acid from (OF test) | |
| glucose aerobic | + |
| glucose anaerobic | + |
| Gas from glucose | + |
| Acid from (ASA) | |
| glucose | + |
| fructose | + |
| xylose | + |
| erythritol | − |
| adonitol | + |
| D-mannose | + |
| L-rhamnose | + |
| dulcitol | − |
| inositol | + |
| sorbitol | + |
| α-methyl-D-glucoside | + |
| cellobiose | + |
| maltose | + |
| lactose | + |
| L-sorbose | − |
| L-fucose | + |
| D-arabitol | + |
| ONPG | + |
| ADH | − |
| LDC | + |
| ODC | − |
| VP | + |
| indole | − |
| H$_2$S production | − |
| Simmons citrate | + |
| phenylalanine deaminase | − |
| urease | − |
| hydrolysis of gelatin | |
| DNA | − |

Scientific description of microorganism DSM 9174 identified as *Klebsiella terrigena*:

| Properties of the strain Cell form | Rods |
|---|---|
| width μm | 0.8–1.0 |
| length μm | 1.0–2.0 |
| Motility | − |
| Gram reaction | − |
| Lysis by 3% KOH | + |
| Aminopeptidase (Cerny) | + |
| Spores | − |
| Oxidase | − |
| Catalase | + |
| Growth anaerobic | + |
| Acid from (OF test) | |
| glucose aerobic | + |
| glucose anaerobic | + |
| Gas from glucose | + |

5 -continued

| Properties of the strain Cell form | Rods |
|---|---|
| Acid from (ASA) | |
| glucose | + |
| fructose | + |
| xylose | + |
| erythritol | − |
| adonitol | + |
| D-mannose | + |
| L-rhamnose | + |
| dulcitol | − |
| inositol | + |
| sorbitol | + |
| α-methyl-D-glucoside | + |
| cellobiose | + |
| maltose | + |
| lactose | + |
| L-sorbose | + |
| L-fucose | + |
| D-arabitol | + |
| 5-ketogluconate | + |
| ONPG | + |
| ADH | − |
| LDC | + |
| ODC | + |
| VP | + |
| indole | − |
| H₂S production | − |
| Simmons citrate | + |
| phenylalanine deaminase | − |
| urease | − |
| hydrolysis of gelatin | − |
| DNA | − |

A preferred process for the preparation of S-α-imino carboxylic acids of the general formula

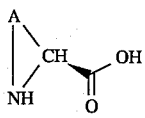

II and/or of R-α-imino carboxamides of the general formula

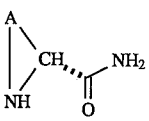

III involves converting the S-α-imino carboxamide in the (RS)-α-amino carboxamide of the general formula

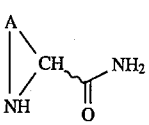

I using the above-described microorganisms, or using cell-free enzymes from these microorganisms, into the S-α-imino carboxylic acid and isolating it, the biotransformation resulting not only in the S-α-imino carboxylic acid but also the R-α-imino carboxamide, which is isolated where appropriate.

The precursors, the (RS)-α-imino carboxamides of the general formula

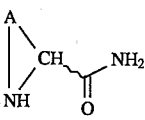

I can be obtained from the corresponding aromatic amides by hydrogenation familiar to the skilled worker.

Imino carboxamides of Formula I with a 5-membered saturated heterocyclic ring which can be used are optionally substituted prolinamide, pyrazolidinecarboxamide, imidazolidinecarboxamide, oxazolidinecarboxamide, isoxazolidinecarboxamide, thiazolidinecarboxamide or triazolidinecarboxamide. Indolinamide can be used, e.g., as substituted prolinamide.

Imino carboxamides of Formula I with a 6-membered saturated heterocyclic ring which can be used are piperazinecarboxamide, pipecolamide, morpholinecarboxamide, perhydroquinolinecarboxamide (quinolinancarboxamide), perhydroisoquinolinecarboxamide (isoquinolinancarboxamide), perhydroquinoxalinecarboxamide (quinoxalinancarboxamide), which are likewise optionally substituted. Representatives of amino carboxamides with a substituted 6-membered saturated heterocyclic ring can be $C_1$-$C_4$-alkyl-substituted, e.g., 4-methylpipecolamide; $H_2N$-$CH_2$-substituted, e.g., 4-aminomethylpipecolamide; or CN-substituted, e.g., 4-cyanopipecolamide. Piperazinecarboxamide, pipecolamide or 4-methylpipecolamide is preferably used.

The enzymes for the cell-free system can be obtained by disruption of the microorganisms, as is familiar to the skilled worker. It is possible to use for this purpose, e.g., the ultrasound, French press or lysozyme method. These cell-free enzymes can also be immobilized on a suitable carrier material.

Particularly suitable for the process are the above-described microorganisms of the species *Klebsiella terrigena* DSM 9174, *Klebsiella pneumoniae* DSM 9175 and DSM 9176, of the species *Pseudomonas putida* DSM 9923 and *Pseudomonas fluorescens* DSM 9924 and their cell-free enzymes. The process can be carried out with the microorganisms or with their functionally equivalent variants and mutants.

The biotransformation can be carried out after conventional cultivation of the microorganisms, using dormant cells (i.e., cells which are not growing and which no longer require a carbon or energy source) or using growing cells.

It is possible to use as medium for the process with dormant cells those familiar to the skilled worker, e.g., the mineral salt medium of Kulla et al., 1983 (ibid.) described above, low-molar phosphate buffer, HEPES buffer or the medium described in Table 1. Normally, a medium containing a carbon source and nitrogen source, e.g., commercially available media or the medium shown in Table 1, is used for the process with growing cells. The process is preferably carried out in the medium shown in Table 1.

The biotransformation is conveniently carried out with a single or with continuous addition of (RS)-α-imino carboxamide in such a way that the concentration of (RS)-α-imino carboxamide does not exceed 20% by weight, preferably 10% by weight.

The pH of the medium can be in a range from pH 5 to pH 11, preferably from pH 7 to pH 10.

The biotransformation is conveniently carried out at a temperature of 25°–65° C., preferably of 30°–60° C.

After a usual reaction time of 1–100 h, the S-α-imino carboxamide of Formula I is completely converted into the S-α-imino carboxylic acid, with R-α-amino carboxamide resulting also.

The S-α-imino carboxylic acid and/or the R-α-amino carboxamide obtained in this way can be isolated by conventional working-up methods, e.g., by acidification, chromatography or extraction.

EXAMPLE 1 a) Isolation of microorganisms capable of utilizing racemic piperazinecarboxamide as sole nitrogen source:

The A-medium whose composition is given in Table 1 was used to isolate microorganisms which are capable of utilizing racemic piperazinecarboxamide as sole nitrogen source. 100 ml of this medium was placed in a 300 ml Erlenmeyer flask, and various soil samples (2 g) from the area of the LONZA AG works in Visp, Switzerland were added. The flasks were incubated without agitation at 30° C. for 5 days. Then 1 ml of this A-medium was used to inoculate a fresh flask containing the same medium. This flask was in turn incubated under the same conditions. This enrichment cycle was repeated a total of 5 times. The enrichments were then streaked onto agar medium (A-medium with the addition of 16 g/l agar) to give single colonies.

The isolated microorganisms were investigated in the following qualitative test system for stereo-selective amidases. Single colonies were used to inoculate 100 ml of A-medium in 300 ml Erlenmeyer flasks. These flasks were incubated on a shaker at 30° C. for 3 days, and the cultures were fully developed after only one day. The cell-free culture supernatants were then investigated by thin-layer chromatography (silica gel, mobile phase: 11 parts of ethanol, 6 parts of $CHCl_3$, 6 parts of $NH_4OH$ (25%), detection with ninhydrin) for the content of piperazinecarboxylic acid and piperazinecarboxamide. Microorganisms which had converted about half the amount of (RS)-piperazinecarboxamide were used for biochemical investigations to establish which strains contained S-specific amidases.

b) Biochemical investigations to identify microorganisms with S-specific amidases:

To prepare crude protein extract, the cells were grown in 1 l of A-medium at 30° C. and then harvested and washed. 5 g of cells (wet weight) was resuspended in 10 ml of 69 mM phosphate buffer, pH 7.0, and disrupted using a FRENCH® press. The crude extract was centrifuged at 40,000×g for 2 h and then frozen in portions at −20° C. To determine the stereoselectivity, the hydrolysis rates for R-prolinamide and S-prolinamide were compared. The following enzyme assay was used for this purpose: assay volume 1 ml, containing 69 mM phosphate buffer, pH 7.0, 100–800 μg crude protein extract, 2 mg of S- or R-prolinamide.HCl, incubation time 1 to 24 h, incubation temperature 30° C., detection with ninhydrin after thin-layer chromatography as described above. These amidases of the strains DSM 9174, DSM 9175 and DSM 9176 show very slow hydrolysis of R-prolinamide. These strains were used to prepare optically active cyclic α-imino-acid derivatives.

Under the same conditions, the crude extracts of the strains DSM 9175 and DSM 9176 showed hydrolysis of (RS)-piperazinecarboxamide and (RS)-pipecolamide. By changing the incubation temperature and the pH of the assay solution, it was found that the specific activity of the amidases was maximal between a temperature of 30°–60° C. and a pH of 7 to 10.

TABLE 1

A-medium:
For this medium, the minimal medium described below was additionally mixed with 2 g/l (RS)-piperazinecarboxamide and 10 g of 10 g/l glycerol.
B-medium:
For this medium, the minimal medium described below was additionally mixed with 1 g/l (RS)-pipecolamide and 4 g/l glucose.
Minimal medium:

| Composition | Concentration (mg/l) |
|---|---|
| Yeast extract | 500 |
| $Na_2SO_4$ | 100 |
| $Na_2HPO_4$ | 2000 |
| $KH_2PO_4$ | 1000 |
| NaCl | 3000 |
| $MgCl_2 \times 6H_2O$ | 400 |
| $CaCl_2 \times 2H_2O$ | 14.5 |
| $FeCl_3 \times 6H_2O$ | 0.8 |
| $ZnSO_4 \times 7H_2O$ | $100 \times 10^{-3}$ |
| $MnCl_2 \times 4H_2O$ | $90 \times 10^{-3}$ |
| $H_3BO_3$ | $300 \times 10^{-3}$ |
| $CoCl_2 \times 6H_2O$ | $200 \times 10^{-3}$ |
| $CuCl_2 \times 2H_2O$ | $10 \times 10^{-3}$ |
| $NiCl_2 \times 6H_2O$ | $20 \times 10^{-3}$ |
| $NaMoO_4 \times 2H_2O$ | $30 \times 10^{-3}$ |
| $EDTA\ Na_2 \times 2H_2O$ | 5 |
| $FeSO_4 \times 7H_2O$ | 2 |

EXAMPLES 2–4

Preparation of S-piperazinecarboxylic acid:

The following conditions were chosen to prepare S-piperazinecarboxylic acid using the strains DSM 9174, DSM 9175 and DSM 9176. A 1.5-liter fermenter equipped with a pH control unit and with a working volume of 1 l was used for the biotransformations. For fermentations in A-medium, the amount of glycerol was increased to 30 g/l and the amount of (RS)-piperazinecarboxamide was increased to 20 g/l. The cells were grown at pH 7.0, a temperature of 30° C. and an aeration rate of 0.5 l/min.

In one case (Example 4) the cells were initially grown under these conditions for 16 hours, and then the temperature was increased to 40° C. and the pH of the medium was increased to 8.0. After predetermined periods of time, the amount of S-piperazinecarboxylic acid formed was estimated by thin-layer chromatography, and the fermentations were stopped after 36 to 72 h, as soon as approximately half of the piperazinecarboxamide had reacted. At this point, the optical densities of the cell suspension at 650 nm were between 6 and 10. To isolate S-piperazinecarboxylic acid, the cell-free solution was concentrated to 100 ml under reduced pressure. The solution was acidified to pH 1.0 with concentrated HCl in order to precipitate the acid as dihydrochloride. The isolated acid was recrystallized in 0.1M HCl and dried. To determine the ee (enantiomeric excess) of the acid formed, the acid was first derivatized with 2,3,4,6-tetra-O-acetyl-β-D-glucopyranosyl isothiocyanate and analyzed by capillary electrophoresis; see Table 2 for the capillary electrophoresis conditions. The results are shown in Table 3.

TABLE 2

Capillary electrophoresis conditions

| | |
|---|---|
| CE apparatus: | Hewlett-Packard HP $^{3D}$CE |
| Detector: | Hewlett-Packard diode array detector |

TABLE 2-continued

Capillary electrophoresis conditions

| | |
|---|---|
| Buffer: | 10 mM disodium hydrogen phosphate, 10 mM boric acid, 150 mM sodium dodecyl sulphate, pH 9.0 |
| Electrolyte: | 900 ml of buffer plus 100 ml of methanol |
| Capillary: | HP G1600-61211 |
| Electric field: | 20 kV |
| Current: | about 24–30 μA |
| Oven temperature: | 20° C. |
| Detector setting: | 210 nm (bandwidth 5 nm) |
| Migration time: | about 17.1 min (S acid) about 17.7 min (R acid) |

TABLE 3

| Example strain | Crude product | Recrystal- lized | Yield | ee value |
|---|---|---|---|---|
| No. 2 DSM 9175 | 12.82 g | 10.74 g | 68.3% | 99.6% |
| No. 3 DSM 9174 | 15.53 g | 13.1 g | 83.3% | 99.4 |
| No. 4 DSM 9176 | 21.23 g | 11.32 g | 72.0% | 99.6 |

EXAMPLE 5

Preparation of S-pipecolic acid using Klebsiella:

Dormant cells of the *Klebsiella Pneumoniae* strains DSM 9175 and DSM 9176 converted 20 g/l (RS)-pipecolamide at 47° C. and a pH of 8.0 into the (S)-acid within 6 h.

When this conversion was carried out with *Klebsiella pneumoniae* DSM 9175, S-pipecolic acid with an ee of 96.5% was obtained.

EXAMPLE 6

Preparation of S-4-methylpipecolic acid

For this conversion, racemic 4-methylpipecolamide (substrate) was converted using the crude protein extracts from *Klebsiella pneumoniae* DSM 9175 or *Klebsiella terrigena* DSM 9174 in analogy to Example 1b. After incubation at pH 8.0 and 47° C. for 24 h, about 50% of the amide used in a 0.2% strength substrate solution was converted, as measured by TLC analysis.

EXAMPLE 7

Isolation of microorganisms which utilize pipecolamide as sole nitrogen source:

100 ml of B-medium was placed in 300 ml Erlenmeyer flasks, and approximately 2 g soil samples were added. The flasks were incubated without agitation at room temperature for 3 days. Subsequently, fresh flasks containing the same medium were treated with 2 ml from the previous cultures and incubated without agitation at 30° for 4 days. This enrichment cycle was repeated a total of 3 times, carrying out the two last steps under sterile conditions. The last step was additionally carried out on a shaker at 140 rpm. The enrichments were then streaked onto B-medium with addition of 16 g/l agar to give single colonies. Then, those colonies were selected whose property of converting (RS)-pipecolamide into pipecolic acid was stable. For this purpose, the cultures were streaked onto nutrient agar and, after growing for a few days, again streaked from the nutrient agar plate onto pipecolamide/glucose plates. The two strains which showed the required stable property were identified after Gram staining and oxidase test with 20 NE API strips. Two Pseudomonas species were identified: *Pseudomonas putida* DSM 9923 and *Pseudomonas fluorescens* DSM 9924.

EXAMPLE 8

Preparation of S-pipecolic acid:

The strains isolated in Example 7 were used to carry out 1% pipecolamide biotransformations (substrate concentration 1%) in 0.1M phosphate buffer at pH 7.0, 30° C. and 130 rpm. The biomass from the precultures was concentrated and taken up in 0.1M phosphate buffer, pH 7.0, in order to obtain a biomass concentration of $OD_{650\,nm}$=10. The mixtures were incubated on a shaker at 130 rpm and 30° C. and samples were taken at various times. The cell-free supernatants were investigated by thin-layer chromatography (silica gel, mobile phase: 11 parts of ethanol, 6 parts of $CHCl_3$, 6 parts of $NH_4OH$ 25%) for the content of remaining amide and pipecolic acid formed. Subsequently, the cell-free supernatants were subjected to HPLC investigation (isothiocyanate derivatization) in order to check the enantiomeric purity of the pipecolic acid formed. The results showed that *Pseudomonas putida* and *Pseudomonas fluorescens* produced S-pipecolic acid with an optical purity of more than 90%. The optimal conditions for the biotransformation with *Pseudomonas putida* were at pH 8.0 and a temperature of 30° C., and for *Pseudomonas fluorescens* at pH 8.0 and 50° C. When the biotransformation was carried out with *Pseudomonas putida*, S-pipecolic acid was obtained with an ee of 95.0%. When the biotransformation was carried out with *Pseudomonas fluorescens*, S-pipecolic acid with an ee of 97.3% was obtained.

EXAMPLE 9

Preparation of S-piperazinecarboxylic acid:

The two isolated strains described in Example 7 for pipecolamide were used to carry out a 1% piperazinecarboxamide biotransformation at pH 7.0, 30° C. and 130 rpm. The cell-free supernatants were likewise investigated for the content of remaining piperazinecarboxamide and piperazinecarboxylic acid formed by thin-layer chromatography. HPLC analysis allowed checking of the optical purity of the piperazinecarboxylic acid formed. When the biotransformation was carried out with *Pseudomonas putida*, S-piperazinecarboxylic acid with an ee of 73.9% was obtained. When the biotransformation was carried out with *Pseudomonas fluorescens*, S-piperazinecarboxylic acid with an ee of 59.5% was obtained.

We claim:

1. A purified microorganism capable of (i) utilizing as sole nitrogen source an α-imino carboxamide in a form selected from the group consisting of the racemate and its optically active isomers, of the general formula

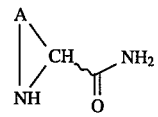

wherein A together with —NH— and —OH— is an optionally substituted 5- or 6-membered saturated heterocyclic ring, and (ii) converting an (RS)-α-imino carboxamide of the Formula I into an S-α-imino carboxylic acid of the general formula

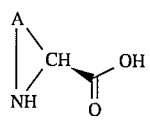

said microorganism being selected from the group consisting of *Pseudomonas putida*, *Pseudomonas fluorescens*, *Klebsiella pneumoniae*, and *Klebsiella terrigena*, and mutants thereof.

2. The microorganism according to claim 1, capable of utilizing as sole nitrogen source one of pipecolamide and piperazinecarboxamide in a form selected from the group consisting of the racemate and its optically active isomers.

* * * * *

UNITED STATES PATENT AND TRADEMARK OFFICE
CERTIFICATE OF CORRECTION

PATENT NO. : 5,622,846

DATED : April 22, 1997

INVENTOR(S) : Andreas Kiener et al.

It is certified that error appears in the above-identified patent and that said Letters Patent is hereby corrected as shown below:

First page of patent, 8th line of ABSTRACT, "carboximides" should read -- carboxamides --; 8th line of ABSTRACT, "S-α-amino" should read -- S-α-imino --; and penultimate line of ABSTRACT, "S-α-amino" should read -- S-α-imino --. Col. 2, line 25, "α-amino" should read -- α-imino --; line 31, "(RS)-α-amino" should read -- (RS)-α-imino --; line 32, "S-α-amino" should read -- S-α-imino --; and line 60, "S-amino-acid" should read -- S-imino-acid --. Col. 5, line 48, "α-amino" should read -- α-imino --. Col. 6, line 62, "R-α-amino" should read -- R-α-imino --. Col. 10, line 65, "—OH—" should read -- —CH— --. Col. 6, line 64, "R-α-amino" should read -- R-α-imino --.

Signed and Sealed this

Seventh Day of April, 1998

Attest:

*Attesting Officer*

BRUCE LEHMAN

*Commissioner of Patents and Trademarks*